United States Patent

Bordes et al.

[54] PREPARATION OF ALIPHATIC CARBOXYLIC ACIDS IN THE PRESENCE OF HETEROPOLYACID CATALYSTS

[75] Inventors: Elisabeth Bordes, Vemars; Michel Gubelmann; Laurent Tessier, both of Paris, all of France

[73] Assignee: Rhone-Poulenc Chimie, Courbevoie Cedex, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/443,450

[22] Filed: May 18, 1995

[30] Foreign Application Priority Data

May 20, 1994 [FR] France ................... 94 06168

[51] Int. Cl.[7] .......................... B01J 27/198; C07C 51/31
[52] U.S. Cl. ................. 502/209; 562/512.2; 562/543; 562/549
[58] Field of Search .................. 562/543, 512.2, 562/549; 502/209

[56] References Cited

U.S. PATENT DOCUMENTS

| | | | |
|---|---|---|---|
| 2,625,519 | 1/1953 | Hartig | 252/432 |
| 4,192,951 | 3/1980 | Slinkard et al. | 562/549 |
| 4,250,346 | 2/1981 | Young et al. | 585/658 |
| 4,410,752 | 10/1983 | Blum et al. | 585/658 |
| 4,689,436 | 8/1987 | Minokani et al. | 585/422 |
| 5,091,354 | 2/1992 | Ellis, Jr. et al. | 502/200 |
| 5,162,578 | 11/1992 | McCain, Jr. et al. | 562/512.2 |
| 5,260,250 | 11/1993 | Kitson | 502/306 |
| 5,300,682 | 4/1994 | Blum et al. | 562/512.2 |
| 5,300,684 | 4/1994 | Benkalowycz et al. | 562/547 |
| 5,334,780 | 8/1994 | Shaikh et al. | 568/910 |
| 5,393,922 | 2/1995 | Sen et al. | 562/542 |
| 5,510,308 | 4/1996 | Kourtakis | 502/209 |

FOREIGN PATENT DOCUMENTS

| | | |
|---|---|---|
| 0294845 | 12/1988 | European Pat. Off. . |
| 0518548 | 12/1992 | European Pat. Off. . |
| 0627401 | 12/1994 | European Pat. Off. . |
| 59-36546 | 2/1984 | Japan . |

*Primary Examiner*—Randy Gulakowski
*Attorney, Agent, or Firm*—Burns, Doane, Swecker & Mathis, L.L.P.

[57] ABSTRACT

The aliphatic carboxylic acids, e.g., acetic acid, are selectively prepared, even on an industrial scale, by controlledly oxidizing the corresponding alkanes, e.g., ethane, with a source of oxygen, in the presence of a catalytically effective amount of an advantageously supported heteropolyacid catalyst having the formula (I):

$$[A_aB_b][C_cD_dE_eO_x]^{f-} \qquad (I)$$

in which A is at least one monovalent cation selected from among hydrogen, an alkali metal, or the ammonium ion; B is $VO^{2+}$, $VO^{3+}$, an alkaline earth metal ion, or an ion of a metal of Groups VII A, VIII, I B, IV B and V B of the Periodic Table; C is Mo and/or W; D is phosphorus, arsenic, antimony, silicon, germanium and/or boron; E is vanadium, optionally in combination with at least one metal of Groups V A, VII A and VIII of the Periodic Table or chromium; $f=a+\alpha b$ wherein $\alpha$ depends on the charge of the ion B, which is equal to 2, 3 or 4; c is a number ranging from 5 to 20-e; d is a number ranging from 1 to 5; and e is a number ranging from 1 to 9.

21 Claims, No Drawings

PREPARATION OF ALIPHATIC CARBOXYLIC ACIDS IN THE PRESENCE OF HETEROPOLYACID CATALYSTS

BACKGROUND OF THE INVENTION

1. Technical Field of the Invention

The present invention relates to the preparation of carboxylic acids by controlled oxidation of the corresponding alkanes, in the presence of heteropolyacid catalysts.

The present invention also relates to novel compositions comprising a heteropolyacid and a titanium dioxide support therefor, as well as to novel catalysts, such compositions comprising the active catalytic phase thereof.

As utilized herein, by the term "heteropolyacid" (or HPA) are intended both heteropolyacids and polyoxometallates.

2. Description of the Prior Art

The preparation of carboxylic acids, in particular acetic acid, via controlled oxidation of the corresponding alkane, such as ethane, is today widely used since it presents the advantage of employing a starting material which is very cost competitive vis-a-vis those employed in existing technologies.

Among the known processes of this type, representative are those employing, other than ethane and oxygen, catalysts based, at least, on the oxides of vanadium, phosphorus and rhenium. The selectivities in respect of acetic acid are on the order of 30% but they remain, however, less than those of the ethylene coproduced. In addition, such a process requires the introduction of large amounts of water and of an inert gas such as helium or nitrogen into the reactor.

Another known process entails reacting the ethane and oxygen in the presence of catalysts based on at least a mixture of the oxides of molybdenum, vanadium, niobium and antimony, or, alternatively, based on the oxides of molybdenum, vanadium, rhenium, antimony, niobium and calcium. The selectivity in respect of acetic acid when using such catalysts is enhanced relative to that attained via the above process. However, the reaction conditions are demanding. Indeed, it is necessary to carry out the oxidation under conditions combining an elevated temperature, namely, on the order of 300° to 400° C., and a high pressure, on the order of 20 to 30 bar. Moreover, the processes for the preparation of such catalysts are difficult to carry out.

It too is known to employ catalysts whose active phase comprises the oxides of vanadium, in the oxidation state (IV), of titanium and/or of phosphorus. When using these catalysts, their performances are of interest in terms of selectivity in respect of acetic acid. However, the starting material feedstream comprises more than 90% of diluent gas, which results in a very low productivity.

SUMMARY OF THE INVENTION

Accordingly, a major object of the present invention is the provision of an improved process for the preparation of aliphatic carboxylic acids, and more particularly acetic acid, by oxidation of an alkane on an industrial scale and which employs catalysts that are readily manufactured.

Briefly, it has now unexpectedly been found that conducting the subject oxidation reaction in the presence of catalysts whose active phase comprises a heteropolyacid of formula (I) below, avoids or conspicuously ameliorates the above disadvantages and drawbacks to date characterizing the state of this art.

DETAILED DESCRIPTION OF BEST MODE AND PREFERRED EMBODIMENTS OF THE INVENTION

More particularly according to the present invention, the subject process combines an enhanced selectivity in respect of the carboxylic acids formed with modest reaction conditions, thus permitting carrying out the reaction on an industrial scale.

In addition, the process according to the invention may be carried out utilizing a large amount of starting material alkane. This represents a significant advantage relative to the known processes employing reaction mixtures comprising large amounts of inert diluent gas. The reason for this is that the alkane, which is only partially converted, may very readily be recycled in the reaction.

Moreover, the process according to the invention is carried out at a lower temperature than those typically employed. Indeed, it is quite surprising that the alkanes, and most particularly ethane, can be activated at temperatures which may be as low as 150° C.–250° C., given the lower reactivity of ethane relative to longer-chain saturated hydrocarbons or, alternatively, given the reactivity of saturated hydrocarbons relative to unsaturated hydrocarbons, which either may or may not be aromatic.

Thus, the process according to the invention comprises the preparation of aliphatic carboxylic acids via controlled oxidation of the corresponding alkanes, with a source of oxygen, in the presence of an effective amount of a catalyst whose active phase includes a heteropolyacid of formula (I):

$$[A_aB_b]_f[C_cD_dE_eO_x]^{f-} \qquad (I)$$

in which A is at least one monovalent cation selected from among hydrogen, an alkali metal or the ammonium ion; B is $VO^{2+}$, $VO^{3+}$, an alkaline earth metal ion or an ion of a metal of Groups VII A, VIII, I B, IV B and V B of the Periodic Table; C is W and/or Mo; D is phosphorus, arsenic, antimony, silicon, germanium or boron; E is an element selected from among vanadium and at least one of the metals of Groups V A, VII A and VIII of the Periodic Table or chromium; $f=a+\alpha b$; with $\alpha$ depending on the charge of the ion B, which is equal to 2, 3 or 4; c is a number ranging from 5 to 20-e, inclusive; d is a number ranging from 1 to 5, inclusive; and e is a number ranging from 1 to 9, inclusive.

By "Periodic Table" is intended that published in the supplement to the bulletin of the French Chemical Society (No. 1—January 1966).

The present invention also features compositions of matter comprising titanium dioxide as a support for the heteropolyacids of formula (I), i.e., $[A_aB_b]_f[C_cD_dE_eO_x]^{f-}$, in which A, B, C, D, E, a, b, c, d, e and f are as defined above.

Too, this invention features novel catalysts comprising the aforesaid compositions as the active catalytic phase thereof.

In the description which follows, the terms titanium dioxide and titanium oxide are intended to be synonymous.

Thus, the process according to the invention is carried out in the presence of a catalytically effective amount of a catalyst whose active phase comprises a heteropolyacid of the above formula (I).

More particularly, the constituent B is advantageously selected from among $VO^{2+}$, $VO^{3+}$, $Cu^{2+}$, $Fe^{3+}$, $Co^{2+}$, $Ag^+$, $Ni^{2+}$, $Mn^{2+}$, $Mg^{2+}$, $Bi^{3+}$, $Sn^{2+}$ and $Sn^{4+}$ ions.

The constituent B is preferably selected from the $VO^{2+}$ and $VO^{3+}$ ions.

As regards the constituent E which is other than vanadium, this is more particularly selected from among chromium, manganese, iron, cobalt and nickel.

In a preferred embodiment of the invention, the heteropolyacid has the formula (I), in which D is phosphorus, E is vanadium, d is equal to 1, c ranges from 1 to 3 and the sum c+e is equal to 12.

In another particular embodiment of the invention, the catalyst employed has an active phase which also comprises a support.

Exemplary such supports include the titanium, silicon, zirconium, cerium and tin dioxides, alumina and silica/alumina, whether used alone or in admixture.

The support is preferably titanium dioxide or zirconium dioxide, with the former being the preferred.

In another embodiment, the active phase of the catalyst has an atomic ratio, (C+E)/metal element of the support, ranging from 0.1% to 30%. By the term "metal element of the support" is intended the titanium, zirconium, cerium, etc.

The aforesaid atomic ratio preferably ranges from 5% to 20%.

In the event that the active phase comprises a support, the distribution between the two constituents of the active phase is such that the heteropolyacid of formula (I) is more particularly dispersed or deposited at the face surfaces of said support.

In a first embodiment, the catalyst is employed in bulk form, namely, it is a catalyst comprising only the active phase obtained from the heteropolyacid and, where appropriate, from the support.

In a second embodiment, the catalyst is employed in a dilute state, i.e., the aforesaid active phase is admixed with an inert material.

In this latter instance, the active phase may either be deposited onto the inert material or coated thereon, or, alternatively, may be intimately mixed therewith.

Exemplary such inert materials include sintered clay, magnesia, magnesium silicate and diatomaceous earth. These types of inert material may be used in porous or non-porous form. The inert material is preferably in non-porous form. If necessary, an enamelling may be carried out in order to render it thus.

The ceramic materials, of the cordierite, mullite, porcelain, silicon nitride, boron nitride and silicon carbide type, may also be used as the inert material.

The catalyst employed in the process according to the invention, which either may or may not be diluted, is advantageously in the form of particles or in monolith form.

If the catalyst is particulate, the size of the particles depends on the mode of use of the catalyst. It may thus vary over a wide range, for example from a few micrometers to about ten millimeters. More particularly, in one embodiment the catalyst comprises a fixed bed and has a particle size distribution generally ranging from 0.5 to 6 mm. The particle size of a catalyst employed in a fluidized or moving bed typically ranges from 5 to 700 microns, and preferably from 5 to 200 microns, for 80% of the particles.

Also if the catalyst is particulate, all forms are suitable for carrying out the process of the invention. Thus, the catalyst may, for example, be in the form of beads or rings. By the term "rings" are intended hollow objects of circular, parallelepipedal and ellipsoid cross section, inter alia. Any other type of complex structure shaped by extrusion of the inert material, for example cross, star, etc., may likewise be employed.

The amount of inert material comprising the composition of the catalyst can vary over a wide range, typically depending on the technique for shaping the catalyst.

Thus, catalysts prepared by coating or depositing the active phase onto the inert material advantageously have an amount of active phase which usually ranges from 0.1% to 30%, and preferably from 2% to 20%, of the total weight of catalyst (active phase+inert material).

In the event that the catalyst comprises the active phase dispersed in an inert material, the amount of active phase advantageously ranges from 1% to 90% of the total weight of the catalyst.

In a preferred embodiment of the invention, the active phase of the catalyst is coated onto the inert material.

The catalyst may be prepared according to any standard, simple and reproducible technique, which constitutes an additional advantage of the invention.

The heteropolyacids are known compounds and processes for the preparation thereof are also well known to this art.

More particularly with respect to the heteropolyacids in which A is a hydrogen atom, two preparative techniques are especially suitable.

According to a first technique, which is more particularly suitable for the preparation of heteropolyacids in which b is equal to 0 and d is equal to 1, a mixture comprising the constituent elements of the heteropolyacid, preferably in oxide form, is maintained at reflux in water for 24 hours.

Another technique for preparing heteropolyacids of the same type as above and in which the value of c ranges from 6 to 12 entails preparing a solution of the constituent elements of the HPA, which are present in the form of alkali metal or alkaline earth metal salts. This solution is obtained by dissolving said compounds in water.

Once the solution is provided, it is neutralized by the addition of an inorganic acid such as hydrochloric acid, in particular. The resulting product is extracted from the medium with ether and then contacted with distilled water to give an aqueous solution, from which the heteropolyacid may be crystallized.

On conclusion of each of these two techniques, the desired heteropolyacid can be recovered by evaporation or crystallization. This product may be used directly as a catalyst in the reaction according to the invention, optionally after having been subjected to a calcination step which will be described below.

In conventional manner and in the event that the catalyst comprises a support, the contacting of the heteropolyacid with the support is carried out by means, for example, of a dry impregnation, although other routes are also envisaged. In this respect, mixing of the various constituents, heteropolyacid and support, in solid form for example, is exemplary.

According to the impregnation technique, the support as described above is contacted with a solution of heteropolyacid in an amount such that the atomic ratio, (C+E)/metal element of the support, ranges from 0.1% to 30% and preferably from 5% to 20%.

The resulting suspension is then dried. This drying step may advantageously be carried out in two stages: the first stage entailing evaporating off the solvent or dispersion medium of the mixture, more particularly the water, to dryness, the second stage entailing drying the paste thus obtained.

Generally, the first step is carried out at a temperature ranging from 20° to 100° C. under vacuum or otherwise, for the time necessary to obtain a paste.

The evaporation is usually carried out with stirring.

The paste obtained is then dried, in a second stage, under an atmosphere which is preferably nonreducing, such as oxygen or air for example, for an average duration of 15 hours.

The drying temperature typically ranges from 100° to 150° C.

It should be appreciated that other drying techniques will suffice, such as, for example, drying of the suspension by spraying in any type of apparatus and under conditions known to this art.

The dried product is then subjected to a calcination step.

This step is performed, in standard fashion, under a nonreducing atmosphere. Air is advantageously used, but oxygen may be employed equally as well.

The calcination temperature advantageously ranges from 200° to 500° C.

The duration of the operation generally ranges from 1 to 24 hours.

Prior to and/or subsequent to the calcination step, the dried product may be subjected to a deagglomeration step.

In the event that the catalyst used in the process according to the invention comprises an inert material, the coating technique is preferably employed.

Thus, the inert material, preferably in the form of coarse particles, and the active phase are placed together in a high shear mixer (LODIGE-type machines) or in a granulation apparatus (granulators, in drum or plate form).

The operation is generally carried out at a temperature ranging from 20° to 150° C. for the period of time necessary to coat the inert material with the desired amount of active phase, more particularly under air, for at least 30 minutes.

The particles thus obtained are typically calcined at a temperature ranging from 300° to 500° C.

The duration of the calcination is generally at least 3 hours.

Of course, all of these techniques for the preparation of the heteropolyacid, and of contacting said HPA with the support and/or the inert material, are exemplary only.

As indicated above, the process according to the invention comprises the controlled oxidation of the alkane with a source of oxygen, in the presence of a catalyst as described above.

There are no specific conditions regarding the quality of the alkane employed. However, for obvious reasons of separation of the acid formed, it is preferred to use ethane having a purity of at least 90%.

The reaction for the controlled oxidation of the alkane is carried out in the presence of a source of oxygen. This source may be based on pure oxygen or oxygen diluted in an inert gas, or, alternatively, may be based on nitrous oxide.

It is thus possible, advantageously, to carry out the oxidation reaction using air as the source of oxygen.

In a specific embodiment of the present invention, the molar ratio between the alkane and the oxygen is less than 20. More particularly, this ratio ranges from 0.01 to 0.2, or from 0.6 to 18.

In a preferred embodiment of the invention, said ratio ranges from 0.6 to 18.

The oxidation reaction may also be carried out in the presence of a diluent.

By the term "diluent" is intended water, or inert gases such as nitrogen, or rare gases such as helium or argon, for example. It should be appreciated that the diluent gases may also be gases recycled from the reaction, such as the oxides of carbon. The diluent gas may be the combination of some or all of the aforesaid gases.

The composition of the gaseous mixture, i.e., of the alkane, the source of oxygen and, where appropriate, the diluent gas, may vary over a wide range.

Except where otherwise indicated, all parts and percentages given below are expressed in molar percent of the gaseous mixture.

In general, the alkane content in the gaseous mixture ranges from 0.1% to 99.9%.

In a specific embodiment of the invention, the composition of the gaseous mixture is such that it is outside the explosive range of the mixture.

More particularly, and in order to provide a gaseous mixture whose composition is suitably without the explosive range, said alkane content ranges from 0.1% to 3% or from 10% to 99%.

The alkane content in the aforesaid gaseous mixture preferably ranges from 10% to 99%.

The oxygen content in the gaseous mixture likewise varies over a wide concentration range. It advantageously ranges from 0.1% to 99.9%.

According to a more specific embodiment, the oxygen content in the gaseous mixture ranges from 1% to 90% or from 97% to 99.9%.

The oxygen contained in said mixture preferably ranges from 1% to 90%.

In another embodiment of the invention, the reaction is carried out in the presence of water. In this event, the water content in the gaseous mixture more particularly ranges from greater than 0% to 70%.

In a specific embodiment thereof, the water content in the aforesaid mixture ranges from 0% to 20%.

The inert gas content in the mixture, nitrogen being the preferred, advantageously ranges from 0% to 70%.

More particularly, the mixture comprises up to 20% of diluent gas.

The gaseous mixture is thus contacted with the catalyst according to the invention.

It should be appreciated that the contacting of the gaseous mixture with the catalyst may be effected by pre-mixing all of the constituents of the mixture beforehand, or, alternatively, by introducing them separately. It is also possible to utilize a multi-stage injection of the alkane or, preferably, of the source of oxygen, into the reactor.

The latter two techniques are preferably employed in the case of industrial-scale operations, for reasons of safety of the process. Indeed, in this manner, the need to remove too large an amount of calories due to the exothermic nature of the reaction is avoided, and the risks of generating compositions within the explosive range of the mixture are reduced.

The apparatus in which the process according to the invention is carried out comprises standard means for catalytic reactions in the gaseous phase; the process may be carried out continuously or discontinuously.

Thus, the reaction may be carried out in a reactor in which the catalyst is in a fixed, fluidized or transported bed, in alternative fixed beds, or, alternatively, in a reverse-flow or countercurrent reactor. The process according to the invention is preferably carried out in fixed, fluidized, or, alternatively, transported bed reactors. In this regard, see the article "Réacteurs Chimiques" ["Chemical Reactors"] by P. Trambouze, published in *Techniques de l'Ingénieur* [Engineering Techniques] (J 4020, 12-1993), as well as the article "Selective oxidation in riser reactor" by R. M. Contractor and A. W. Sleight, published in *Catalysis Today* (vol. 3 (1988), 175–184), relating more particularly to transported bed reactors.

The reaction temperature advantageously ranges from 100° to 400° C., preferably from 150° to 350° C.

The total pressure of the gaseous reaction mixture generally ranges from 0.1 to 20 bar absolute.

The gas flow rate is established such that the contact time, calculated under standard temperature and pressure conditions, ranges from 0.1 to 30 seconds.

The contact time preferably ranges from 0.5 to 20 seconds. It will be appreciated that the contact time corresponds to the ratio between the volume of the reactor and the total flow rate of the gases.

The final product carboxylic acid is separated from the byproducts or from the reactants in conventional manner by cooling and condensation of an acid/water mixture.

The compounds remaining in gaseous form, more particularly the alkane and the carbon oxides, may, advantageously, be recycled into the reactor. Recycling of the alkane is of apparent advantage to one skilled in this art, this advantage being to minimize the losses of reactant. It should, however, also be appreciated that recycling of the alkane and the oxides of carbon presents an additional advantage, relating to the absorption of calories released during the oxidation reaction. Indeed, these gases have considerable heat capacities which render same particularly suitable for this purpose and, consequently, the fact that they are recycled permits minimizing the risks of a local increase in the temperature (hot spots).

In the event of recycling these gases, and more especially as regards the oxides of carbon, it is known to this art to regularly purge these gases, which may well accumulate over the course of the recycling operations.

The compositions according to the invention will now be more fully described.

These compositions comprise a titanium dioxide support and a heteropolyacid of formula (I) as described above.

In a preferred embodiment of the invention, the heteropolyacid corresponds to the formula (I) in which D is phosphorus, E is vanadium, c ranges from 1 to 3, inclusive, d is equal to 1, and the sum c+e is equal to 12.

The titanium oxide present in the catalyst of the invention may be in the form of anatase, rutile, brookite or, alternatively, bronze $TiO_2$ (symbolized (B)), or mixtures thereof.

The allotropic form of the titanium oxide is preferably selected from the anatase and rutile forms, or mixtures thereof.

The titanium oxide formulated in the composition of the active phase also has a specific surface, measured according to the B.E.T. method, ranging from 1 to 150 $m^2/g$. The specific surface more particularly ranges from 10 to 120 $m^2/g$.

The compositions according to the invention are more particularly such that the atomic ratio (C+E)/Ti ranges from 0.1% to 30% and preferably from 5% to 20%.

Too, the present invention features catalysts whose active phase is the composition described above.

In a preferred embodiment, the catalysts according to the invention comprise an inert material, other than the active phase derived from titanium dioxide and a heteropolyacid of formula (I).

A first embodiment thereof comprises a catalyst of coated type. In this event, the amount of composition according to the invention ranges from 0.1% to 30% by weight, relative to the total weight of the catalyst. This content preferably ranges from 2% to 20% by weight.

A second embodiment entails a catalyst whose active phase is dispersed in the inert material. According to this embodiment, the amount of composition ranges from 1% to 90% by weight, relative to the total weight of the catalyst.

In order to further illustrate the present invention and the advantages thereof, the following specific examples are given, it being understood that same are intended only as illustrative and in nowise limitative.

In said examples to follow, the catalysts were evaluated in the following manner:

The conversion was calculated from the sum of the yields of products obtained:

(a) Conversion of Ethane (% mol)

$$\text{Conv. ethane} = \frac{\Sigma \text{ nbr of moles of products} \times \text{ obtained}}{(\text{nbr moles of ethane introduced})} \times 100$$

(b) Selectivity for a Product X (Acetic Acid, Ethylene, Combustion Products) (mol %)

$$\text{Sel. } X = \frac{\text{nbr of moles of product } X}{\Sigma \text{ nbr of moles of products } X \text{ obtained}} \times 100$$

EXAMPLE 1

Synthesis of a Heteropolyacid of Formula $H_4PMo_{11}VO_{40}/TiO_2$ (Catalyst 1)

8.23 g of $MoO_3$, 0.52 g of $V_2O_5$ and 0.66 g of 85% $H_3PO_4$ were mixed together in 150 ml of distilled water. After refluxing for 24 hours, 30 g of anatase $TiO_2$ (DT 51, Rhône-Poulenc-86 $m^2/g$) were added to the purple-red solution and the mixture was evaporated to dryness under vacuum.

The product was calcined at 320° C. under air for 4 hours.

A catalyst was obtained wherein the ratio (Mo+V)/Ti was 16.7%.

$^{31}$p magic angle Nuclear Magnetic Resonance analysis (unit: shift in ppm relative to an external reference of aqueous 85% $H_3PO_4$ solution). This analysis permitted confirmation that the structure of the HPA was at least partially retained.

This technique gave signals between −3 and −4 ppm (singlet) for the bulk HPA in weak interaction with the $TiO_2$ support; at about +2 ppm (singlet) for the HPA in strong interaction with the $TiO_2$, support; between −10 and −15 ppm (broad poorly resolved signal) for the decomposed HPA. It should be appreciated that the presence of a signal between −3 and −4 ppm after synthesis of the catalyst is important in order to obtain good catalytic performances.

EXAMPLE 2

Synthesis of a Heteropolyacid of Formula $H_5PMo_{10}V_2O_{40}$ (Catalyst 2)

The sodium salts of the various constituents were employed in the following proportions:

(i) 1 mol of $Na_2MoO_4 \cdot 2H_2O$ (242.0 g), (ii) 0.4 mol of $NaVO_3$ (48.8 g), (iii) 0.1 mol of $Na_2HPO_4$ (14.1 g).

(a) $NaVO_3$ was dissolved in 500 ml of boiling water. $Na_2HPO_4$ was added and the mixture was permitted to cool.

(b) $Na_2MoO_4 \cdot 2H_2O$ was dissolved in 500 ml of cold water.

(c) Solution (a) was acidified with 37% HCl until a purple-red color was obtained, and solution (b) was then added rapidly thereto, followed by dropwise addition of 400 ml of 37% HCl while cooling in an ice bath.

(d) The etherate of the acid $H_5PMo_{10}V_2O_{40}$ was collected by extraction of solution (c) with ether.

3 phases existed in the separating funnel:

lower: etherate of the acid, middle: orange-colored aqueous phase, upper: ether.

The etherate was hydrolyzed using half its volume of water and the mixture was permitted to crystallize at 4° C.

The crystals of $H_5PMo_{10}V_2O_{40}.nH_2O$ obtained were calcined at 320° C. under air.

EXAMPLE 3

Synthesis of a Heteropolyacid of Formula $H_5PMo_{10}V_2O_{40}TiO_2$ (Catalyst 3)

9.08 g of the heteropolyacid obtained in Example 2 were dissolved in 150 ml of water with 14 g of 50% $H_2O_2$.

30 g of $TiO_2$ in anatase form (DT 51, Rhône-Poulenc-86 m²/g) were then added and the mixture was evaporated to dryness under vacuum.

The product was dried for 16 hours at 140° C. and then calcined under air at 320° C. for 4 hours.

A catalyst was obtained wherein the ratio (Mo+V)/Ti was 16.7%.

EXAMPLE 4

Synthesis of a Heteropolyacid of Formula $H_6PMo_9V_3O_{40}$ (Catalyst 4)

The procedure of Example 2 was repeated, but employing the following proportions:

(i) 0.45 mol of $Na_2MoO_4.2H_2O$ (108.90 g)
(ii) 0.6 mol of $NaVO_3$ (73.20 g),
(iii) 0.1 mol of $Na_2HPO_4$ (14.2 g)

A catalyst was obtained wherein the ratio (Mo+V)/Ti was 16.7%.

EXAMPLE 5 (Comparative)

Synthesis of a Heteropolyacid of Formula $H_3PMo_{12}O_{40}/TiO_2$ (Catalyst 5)

The procedure of Example 3 was repeated, but using commercial $H_3PMo_{12}O_{40}.nH_2O$ (Fluka).

The product was calcined at 320° C. under air for 4 hours.

A catalyst was obtained whose ratio Mo/Ti was 16.7%.

EXAMPLE 6

This example illustrates the performances of the catalysts described above in the reaction for the controlled oxidation of ethane into acetic acid.

3 g of catalyst powder were introduced into a stainless steel fixed bed continuous reactor equipped with heating means via a bath of fluidized sand and with two chromatographs in series, one operating with a flame ionization detector and the other with a thermoconductimetric detector.

The feed gases were controlled by mass flowmeters.

The feed flow (expressed in mol %) was:

ethane/$O_2$/$N_2$=85/5/10.
The hourly volume rate was 3,200 h$^{-1}$.
The pressure of the reactor was maintained constant at 1 or 11 bar absolute.
The temperature was 250° C.

The results obtained are reported in the following Table:

TABLE

| Catalyst | P (bar absolute) | Conv. ethane (%) | Sel. AcOH (%) | Sel. $C_2H_4$ (%) | Sel. $CO_x$ (%) |
|---|---|---|---|---|---|
| 1 | 1 | 0.5 | 69 | 21 | 10 |
| 2 | 11 | 0.5 | 65 | 30 | 5 |
| 3 | 1 | 0.6 | 61 | 26 | 13 |
| 4 | 11 | 0.4 | 78 | 17 | 5 |
| 5 | 1 | 0.1 | 50 | 39 | 11 |

It will be appreciated that the theoretical conversion of ethane into acetic acid is 3.9%.

EXAMPLE 7

This example illustrates the performances of the catalyst No. 1.

The conditions of reaction were those described in Example 6, except that the feed flow [expressed in mol %] was:

ethane/$O_2$/$H_2O$/$N_2$=62/17/10/11

The hourly volume rate was 2,400 h$^{-1}$.
The pressure of the reactor was 6 bar absolute.
The temperature was 275° C.

Under such conditions, the conversion of ethane was 7.7%.

The selectivity in respect of acetic acid was 70%, the selectivity in respect of ethane was 10% and the selectivity in respect of $CO_x$ was 20%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of acetic acid, comprising controlledly oxidizing ethane with a source of oxygen, in the presence of a catalytically effective amount of a heteropolyacid catalyst having the formula (I):

$$[A_aB_b]_f[C_cD_dE_eO_x]^{f-} \qquad (I)$$

in which A is at least one monovalent cation selected from among hydrogen, an alkali metal, or the ammonium ion; B is $VO^{2+}$, $VO^{3+}$, an alkaline earth metal ion, or an ion of a metal of Groups VII A, VIII, I B, IV B and V B of the Periodic Table; C is Mo and/or W; D is phosphorus, arsenic, antimony, silicon, germanium and/or boron; E is vanadium, optionally in combination with at least one metal of Groups V A, VII A and VIII of the Periodic Table or chromium; f=a+αb wherein α is the charge of the ion B, which charge is equal to 2, 3 or 4; a and b are non-negative numbers; c is a number ranging from 5 to 20-e; d is a number ranging from 1 to 5; and e is a number ranging from 1 to 9, thereby forming acetic acid.

2. The process as defined by claim 1, wherein formula (I), D is phosphorus, E is vanadium, c ranges from 1 to 3, d is 1 and the sum c+e is 12.

3. The process as defined by claim 1, said active heteropolyacid catalyst comprising a support therefor.

4. The process as defined by claim 3, said support comprising titanium dioxide.

5. The process as defined by claim 1, said starting material ethane comprising gaseous mixture containing from 0.1 to 99.9 mol % thereof.

6. The process as defined by claim 5, said gaseous mixture containing from 0.1 to 3 mol % of said starting material ethane.

7. The process as defined by claim 5, said gaseous mixture containing from 10 to 99 mol % of said starting material ethane.

8. The process as defined by claim 1, said source of oxygen comprising air, oxygen or nitrous oxide.

9. The process as defined by claim 5, said gaseous mixture comprising from 0.1 to 99.9 mol % of oxygen.

10. The process as defined by claim 9, said gaseous mixture comprising from 1 to 90 mol % of oxygen.

11. The process as defined by claim 9, said gaseous mixture comprising from 97 to 99.9 mol % of oxygen.

12. The process as defined by claim 9, said gaseous mixture having an alkane/oxygen molar ratio of less than 20.

13. The process as defined by claim 12, said molar ratio ranging from 0.01 to 0.2.

14. The process as defined by claim 12, said molar ratio ranging from 0.6 to 18.

15. The process as defined by claim 9, said gaseous mixture comprising a diluent selected from among water, an inert gas, a gas recycled from the oxidation reaction, or mixture thereof.

16. The process as defined by claim 15, said diluent comprising water.

17. The process as defined by claim 15, said diluent comprising a rare gas or nitrogen.

18. The process as defined by claim 15, said gaseous mixture comprising up to 70 mol % of an inert gas.

19. The process as defined by claim 18, said gaseous mixture comprising up to 20 mol % of an inert gas.

20. The process as defined by claim 11, wherein formula (I), B is selected from among $VO^{2+}$, $VO^{3+}$, $Cu^{2+}$, $Fe^{3+}$, $Co^{2+}$, $Ag^+$, $Ni^{2+}$, $Mn^{2+}$, $Mg^{2+}$, $Bi^{3+}$, $Sn^{2+}$ and $Sn^{4+}$ ions.

21. A process for the preparation of acetic acid, comprising controlledly oxidizing ethane with a source of oxygen, in the presence of a catalytically effective amount of a heteropolyacid catalyst having the formula (I):

$$[A_aB_b]_f[C_cD_dE_eO_x]^{f-} \qquad (I)$$

in which A is at least one monovalent cation selected from among hydrogen, an alkali metal, or the ammonium ion; B is $VO^{2+}$, $VO^{3+}$, an alkaline earth metal ion, or an ion of a metal of Groups VII A, VIII, I B, IV B and V B of the Periodic Table; C is Mo and/or W; D is phosphorus, arsenic, antimony, silicon, germanium and/or boron; E is vanadium, optionally in combination with at least one metal of Groups V A, VII A and VIII of the Periodic Table or chromium; f=a+αb wherein α is the charge of the ion B, which charge is equal to 2, 3 or 4; a and b are non-negative numbers; c is a number ranging from 5 to 20-e; d is a number ranging from 1 to 5; and e is a number ranging from 1 to 9, thereby forming acetic acid, said active heteropolyacid catalyst comprising a support therefor, said support comprising an oxide of titanium, silicon, zirconium, cerium or tin, alumina or silica/alumina, or mixture thereof.

* * * * *